US008241619B2

(12) United States Patent
Cheng et al.

(10) Patent No.: US 8,241,619 B2
(45) Date of Patent: Aug. 14, 2012

(54) HINDERED AMINE NITRIC OXIDE DONATING POLYMERS FOR COATING MEDICAL DEVICES

(75) Inventors: Peiwen Cheng, Santa Rosa, CA (US); Mingfei Chen, Santa Rosa, CA (US); Kishore Udipi, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 925 days.

(21) Appl. No.: 11/383,257

(22) Filed: May 15, 2006

(65) Prior Publication Data
US 2007/0264225 A1 Nov. 15, 2007

(51) Int. Cl.
*A61K 31/74* (2006.01)
(52) U.S. Cl. .................................... 424/78.17
(58) Field of Classification Search .................. None
See application file for complete search history.

(56) References Cited

U.S. PATENT DOCUMENTS

| | | |
|---|---|---|
| 4,954,526 A | 9/1990 | Keefer |
| 5,039,705 A | 8/1991 | Keefer et al. |
| 5,155,137 A | 10/1992 | Keefer et al. |
| 5,212,204 A | 5/1993 | Keefer et al. |
| 5,250,550 A | 10/1993 | Keefer et al. |
| 5,268,465 A | 12/1993 | Bredt et al. |
| 5,362,718 A | 11/1994 | Skotnicki et al. |
| 5,366,997 A | 11/1994 | Keefer et al. |
| 5,380,758 A | 1/1995 | Stamler et al. |
| 5,405,919 A | 4/1995 | Keefer et al. |
| 5,428,070 A | 6/1995 | Cooke et al. |
| 5,468,630 A | 11/1995 | Billiar et al. |
| 5,525,357 A | 6/1996 | Keefer et al. |
| 5,574,068 A | 11/1996 | Stamler et al. |
| 5,583,101 A | 12/1996 | Stamler et al. |
| 5,650,447 A | 7/1997 | Keefer et al. |
| 5,658,565 A | 8/1997 | Billiar et al. |
| 5,665,077 A | 9/1997 | Rosen et al. |
| 5,718,892 A | 2/1998 | Keefer et al. |
| 5,891,459 A | 4/1999 | Cooke et al. |
| 5,900,246 A | 5/1999 | Lambert |
| 5,945,452 A | 8/1999 | Cooke et al. |
| 6,015,815 A | 1/2000 | Mollison |
| 6,110,453 A | 8/2000 | Keefer et al. |
| 6,153,588 A | 11/2000 | Chrzan et al. |
| 6,290,981 B1 | 9/2001 | Keefer et al. |
| 6,329,386 B1 | 12/2001 | Mollison |
| 6,403,759 B2 | 6/2002 | Stamler et al. |
| 6,610,660 B1 | 8/2003 | Saavedra et al. |
| 6,673,891 B2 | 1/2004 | Stamler et al. |
| 6,706,274 B2 | 3/2004 | Herrmann et al. |
| 6,737,447 B1 | 5/2004 | Smith et al. |
| 6,759,430 B2 | 7/2004 | Anggard et al. |
| 6,841,166 B1 | 1/2005 | Zhang et al. |
| 6,875,840 B2 | 4/2005 | Stack et al. |
| 6,911,478 B2 | 6/2005 | Hrabie et al. |
| 6,949,530 B2 | 9/2005 | Hrabie et al. |
| 6,951,902 B2 | 10/2005 | McDonald et al. |
| 7,070,798 B1 | 7/2006 | Michal et al. |
| 7,087,709 B2 | 8/2006 | Stamler et al. |
| 7,105,502 B2 | 9/2006 | Arnold et al. |
| 7,378,105 B2 | 5/2008 | Burke et al. |
| 2002/0094985 A1 | 7/2002 | Herrmann et al. |
| 2004/0037836 A1 | 2/2004 | Stamler et al. |
| 2004/0171589 A1 | 9/2004 | Herrmann et al. |
| 2004/0180131 A1 | 9/2004 | Cheng |
| 2005/0171596 A1 | 8/2005 | Furst et al. |
| 2005/0203069 A1 | 9/2005 | Arnold et al. |
| 2005/0265958 A1 | 12/2005 | West et al. |
| 2005/0281866 A1 | 12/2005 | Jarrett et al. |
| 2006/0008529 A1 | 1/2006 | Meyerhoff et al. |
| 2006/0099235 A1 | 5/2006 | Blakstvedt et al. |
| 2006/0121089 A1 | 6/2006 | Michal et al. |
| 2006/0195142 A1 | 8/2006 | Shalaby |
| 2006/0251824 A1 * | 11/2006 | Boulais et al. ................. 427/458 |
| 2007/0014828 A1 | 1/2007 | Fitzhugh et al. |
| 2007/0053952 A1 | 3/2007 | Chen et al. |
| 2007/0185561 A1 | 8/2007 | Schmitz et al. |
| 2008/0220040 A1 | 9/2008 | Cheng et al. |
| 2008/0220048 A1 | 9/2008 | Chen et al. |
| 2009/0028966 A1 | 1/2009 | Chen et al. |
| 2009/0222088 A1 | 9/2009 | Chen et al. |
| 2009/0232863 A1 | 9/2009 | Cheng et al. |
| 2009/0232868 A1 | 9/2009 | Chen et al. |

FOREIGN PATENT DOCUMENTS

| | | |
|---|---|---|
| EP | 0945148 A1 * | 9/1999 |
| EP | 0992252 | 4/2000 |
| EP | 1300424 | 4/2003 |
| WO | WO95/24908 | 9/1995 |
| WO | WO96/15797 | 5/1996 |
| WO | WO99/01427 | 1/1999 |
| WO | WO01/10344 | 2/2001 |
| WO | WO2005/039664 | 5/2005 |
| WO | WO2005/081752 | 9/2005 |
| WO | WO2006/037105 | 4/2006 |
| WO | WO2007/024501 | 3/2007 |

(Continued)

OTHER PUBLICATIONS

Reynolds et al., "Mitric Oxide Releasing Polyurethanes with Covalently Linked Diazeniumdiolated Secondary Amines" Biomacromolecules, vol. 7, Feb. 25, 2006, pp. 987-994. U.S. Appl. No. 12/340,089, filed Dec. 19, 2008.
U.S. Appl. No. 12/422,425, filed Apr. 13, 2009.
Washington State Univ. Lecture, Chemistry 240, Summer 2001, http://chemistry2.csudh.edu/rpendarvis/aminrxn.html.
Tashiro et al., "Removal of Methyl Orange by Systems of Insoluble Poly(Glycidyl Methacrylate)-G-Tetraethylene-Pentamine and -G-Polyethyleneimines", Research Institute for Polymers and Textiles, 205 (1993) 31-45.
Hrabie et al., "New Nitric Oxide-Releasing Zwitterions Derived from Polyamines" J. Org. Chem, 1993, 58, 1472-1476.

(Continued)

Primary Examiner — Paul Dickinson

(57) ABSTRACT

Disclosed are hindered amine nitric oxide (NO) donating polymers for coating implantable medical devices. The polymers include sterically hindered secondary amines that do not react with monomer carbonyls or electrophilic alkenes, facilitating the synthesis of the NO donating polymers. The polymers are coated on implantable medical devices, providing anti-restenosis therapy by the release of NO at the implantation site.

19 Claims, No Drawings

FOREIGN PATENT DOCUMENTS

| WO | WO2007/053292 | 5/2007 |
|---|---|---|
| WO | WO2007/053578 | 5/2007 |

OTHER PUBLICATIONS

Drago et al., "The Reaction of Notrogen(II) Oxide with Diethylamine" Contribution from the W.A. Noyes Laboratory, University of Illinois, Jun. 24, 1959.

Parzuchowski et al., "Synthesis of Potentially More Blood Compatible Nitric Oxide Releasing Acrylic Copolymers" Polymer Preprints, 2001, 42(1), pp. 448-449.

Williams et al. "Nitric Oxide-Releasing Nonsteroidal Anti-Inflammatory Drugs (NSAIDs) Alter the Kinetics of Human Colon Cancer Cell Lines More effectively then Traditional NSAIDs: Implications for Colon Cancer Chemoprevention" Cancer Research, 61, 3285-3289, Apr. 15, 2001, pp. 3285-3289.

Frost et al. "Polymers Incorporating Nitric Oxide Releasing/Generating Substances for Improved Biocompatibility of Blood-Contacting Medical Devices" Biomaterials 26 (2005) 1685-1693.

Deng et al., "Polymerization of Lactides and Lactones 11. Ring-Opening Polymerization of x-Acetyl-y-Butyrolactone and Copolymerization with B-Butyrolactone" European Polymer Journal, 36 (2000) 2739-2741.

Lovric et al., "Scope and Limitations of Sodium and Potassium Trimethylsilanolate as Reagents fro Conversion of Esters to Carboxylic Acids" Croatica Chemica Acta, CCACAA 80 (1), 109-115 (2007).

Kireev et al., "Polymerization of Methyl Methacrylate and Vinyl Acetate Initiated by the Manganese Carbonyl-1,2-Epoxy-4,4,4-Trichlorobutance System" Polymer Science, Ser. B, 2006, vol. 48, Nos. 5-6, pp. 138-141.

Liu et al., "Diethylenetriamine-Grafted Poly(Glycidyl Methacrylate) Adsorbent for Effective Copper Ion Adsorption" Journal of Colloid and Interface Science 303 (2006) 99-108.

Oh et al., "Spontaneous Catalytic Generation of Nitric Oxide from S-Nitrosothiols at the Surface of Polymer Films Doped with Lipophilic Copper (II) Complex" J. Am. Chem. Soc. 203, 125, pp. 9552-9553, 2003.

Abizaid, Alexandre MD "Novel Approaches to New DES Therapies: Where are we Going?" ACC 2007, New Orleans.

Pasterkamp et al., "Atherosclerotic Plaque Rupture: an Overview" J Clin Basic Cardiol, 2000; 3: pp. 81-96.

Wolfe et al., "Cyclic Hydroxamates, Especially Multiply Substituted [1,2] Oxazinan-3-Ones" Can. J. Chem. 81: 937-960 (2003).

* cited by examiner

HINDERED AMINE NITRIC OXIDE DONATING POLYMERS FOR COATING MEDICAL DEVICES

FIELD OF THE INVENTION

The present invention relates to nitric oxide (NO) donating polymers for fabricating and coating medical devices.

BACKGROUND OF THE INVENTION

Since the 19$^{th}$ century, organic nitrate and nitrite esters have found use in the medical community. While the discovery of nitric oxide (NO) as a therapeutically active molecule over 120 years ago (circa 1867) was advantageous, recent research efforts aimed at effective NO delivery have produced numerous methods. Drugs donating NO after biological decomposition have found use in various disorders, for example nitroglycerin alleviates discomfort in patients with ischemic heart disease. In anti-thrombogenic medical applications, NO plays a role in platelet inhibition.

Nitric oxide (NO) is a simple diatomic molecule that plays a diverse and complex role in cellular physiology. Less than 25 years ago NO was primarily considered a smog component formed during the combustion of fossil fuels mixed with air. However, as a result of the pioneering work of Ferid Murad et al. it is now known that NO is a powerful signaling compound and cytotoxic/cytostatic agent found in nearly every tissue including endothelial cells, neural cells and macrophages. Mammalian cells synthesize NO using a two step enzymatic process that oxidizes L-arginine to N-ω-hydroxy-L-arginine, which is then converted into L-citrulline and an uncharged NO free radical. Three different nitric oxide synthase enzymes regulate NO production. Neuronal nitric oxide synthase (NOSI, or nNOS) is formed within neuronal tissue and plays an essential role in neurotransmission; endothelial nitric oxide synthase (NOS3 or eNOS), is secreted by endothelial cells and induces vasodilatation; inducible nitric oxide synthase (NOS2 or iNOS) is principally found in macrophages, hepatocytes and chondrocytes and is associated with immune cytotoxicity.

Neuronal NOS and eNOS are constitutive enzymes that regulate the rapid, short-term release of small amounts of NO. In these minute amounts NO activates guanylate cyclase which elevates cyclic guanosine monophosphate (cGMP) concentrations which in turn increase intracellular $Ca^{+2}$ levels. Increased intracellular $Ca^{+2}$ concentrations results in smooth muscle relaxation which accounts for NO's vasodilating effects. Inducible NOS is responsible for the sustained release of larger amounts of NO and is activated by extracellular factors including endotoxins and cytokines. These higher NO levels play a key role in cellular immunity.

Medical research is rapidly discovering therapeutic applications for NO including the fields of vascular surgery and interventional cardiology. Procedures used to clear blocked arteries such as percutaneous transluminal coronary angioplasty (PTCA) (also known as balloon angioplasty) and atherectomy and/or stent placement can result in vessel wall injury at the site of balloon expansion or stent deployment. In response to this injury a complex multi-factorial process known as restenosis can occur whereby the previously opened vessel lumen narrows and becomes re-occluded. Restenosis is initiated when thrombocytes (platelets) migrating to the injury site release mitogens into the injured endothelium. Thrombocytes begin to aggregate and adhere to the injury site initiating thrombogenesis, or clot formation. As a result, the previously opened lumen begins to narrow as thrombocytes and fibrin collect on the vessel wall. In a more frequently encountered mechanism of restenosis, the mitogens secreted by activated thrombocytes adhering to the vessel wall stimulate overproliferation of vascular smooth muscle cells during the healing process, restricting or occluding the injured vessel lumen. The resulting neointimal hyperplasia is the major cause of a stent restenosis.

Recently, NO has been shown to significantly reduce thrombocyte aggregation and adhesion; this combined with NO's directly cytotoxic/cytostatic properties may significantly reduce vascular smooth muscle cell proliferation and help prevent restenosis. Thrombocyte aggregation occurs within minutes following the initial vascular insult and once the cascade of events leading to restenosis is initiated, irreparable damage can result. Moreover, the risk of thrombogenesis and restenosis persists until the endothelium lining the vessel lumen has been repaired. Therefore, it is essential that NO, or any anti-restenotic agent, reach the injury site immediately.

One approach for providing a therapeutic level of NO at an injury site is to increase systemic NO levels prophylactically. This can be accomplished by stimulating endogenous NO production or using exogenous NO sources. Methods to regulate endogenous NO release have primarily focused on activation of synthetic pathways using excess amounts of NO precursors like L-arginine, or increasing expression of nitric oxide synthase (NOS) using gene therapy. U.S. Pat. Nos. 5,945,452, 5,891,459 and 5,428,070 describe sustained NO elevation using orally administrated L-arginine and/or L-lysine. However, these methods have not been proven effective in preventing restenosis. Regulating endogenously expressed NO using gene therapy techniques remains highly experimental and has not yet proven safe and effective. U.S. Pat. Nos. 5,268,465, 5,468,630 and 5,658,565, describe various gene therapy approaches.

Exogenous NO sources such as pure NO gas are highly toxic, short-lived and relatively insoluble in physiological fluids. Consequently, systemic exogenous NO delivery is generally accomplished using organic nitrate prodrugs such as nitroglycerin tablets, intravenous suspensions, sprays and transdermal patches. The human body rapidly converts nitroglycerin into NO; however, enzyme levels and co-factors required to activate the prodrug are rapidly depleted, resulting in drug tolerance. Moreover, systemic NO administration can have devastating side effects including hypotension and free radical cell damage. Therefore, using organic nitrate prodrugs to maintain systemic anti-restenotic therapeutic blood levels is not currently possible.

Therefore, considerable attention has been focused on localized, or site specific, NO delivery to ameliorate the disadvantages associated with systemic prophylaxis. Implantable medical devices and/or local gene therapy techniques including medical devices coated with NO-releasing compounds, or vectors that deliver NOS genes to target cells, have been evaluated. Like their systemic counterparts, gene therapy techniques for the localized NO delivery have not been proven safe and effective. There are still significant technical hurdles and safety concerns that must be overcome before site-specific NOS gene delivery will become a reality.

However, significant progress has been made in the field of localized exogenous NO application. To be effective at preventing restenosis an inhibitory therapeutic such as NO must be administered for a sustained period at therapeutic levels. Consequently, any NO-releasing medical device used to treat restenosis must be suitable for implantation. An ideal candidate device is the vascular stent. Therefore, a stent that safely provides therapeutically effective amounts of NO to a precise location would represent a significant advance in restenosis treatment and prevention.

Nitric oxide-releasing compounds suitable for in vivo applications have been developed by a number of investigators. As early as 1960 it was demonstrated that nitric oxide gas could be reacted with amines, for example, diethylamine, to form NO-releasing anions having the following general formula R—R'N—N—(O)NO. Salts of these compounds could spontaneously decompose and release NO in solution. (R. S. Drago et al., J. Am. Chem. Soc. 1960, 82:96-98)

Nitric oxide-releasing compounds with sufficient stability at body temperatures to be useful as therapeutics were ultimately developed by Keefer et al. as described in U.S. Pat. Nos. 4,954,526, 5,039,705, 5,155,137, 5,212,204, 5,250,550, 5,366,997, 5,405,919, 5,525,357 and 5,650,447 and in J. A. Hrabie et al., J. Org. Chem. 1993, 58:1472-1476, all of which are herein incorporated by reference.

The in vivo half-life of NO, however, is limited, causing difficulties in delivering NO to the intended area. Therefore NO-releasing compounds which can produce extended release of NO are needed. Several exemplary NO-releasing compounds have been developed for this purpose, including for example a NO donating aspirin derivative, (Formula 1, *Cancer Research,* 2001, 61, pp 3285-3289), amyl nitrite and isosorbide dinitrate. Additionally, biocompatible polymers having NO adducts (see, for example, U.S. Patent Publications 2006/0008529 and 2004/0037836) and which release NO in a controlled manner have been reported.

Formula 1

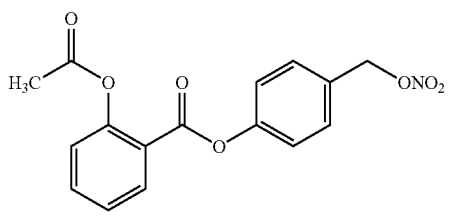

Secondary amines have the ability to bind two NO molecules and release them in an aqueous environment. The general structure of an exemplary secondary amines capable of binding two NO molecules is depicted in Formula 2 (wherein M is a counterion, and can be a metal, with the appropriate charge, or a proton and wherein R is a generic notation for organic and inorganic chemical groups), and referred to hereinafter a diazeniumdiolate. Exposing the secondary amine to basic conditions while incorporating NO gas under high pressure leads to the formation of diazeniumdiolates.

Formula 2

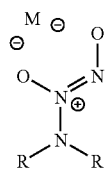

Acrylic polymers containing a plurality of secondary amines having NO molecules incorporated have been synthesized and diazeniumdiolates formed (see for example, *J. Am. Chem. Soc.,* 2002, 124, pp 12182-12191). In the synthesis of the polymers in the aforementioned reference, protection and de-protection steps of amines were utilized because of the reactive nature of amines with unsaturated groups present such as carbonyl groups or electron deficient alkenes. Sterically hindering the amines in the polymers reduces their ability to react with unsaturated groups. Applicants have determined that biocompatible polymers based on these hindered amines provide local NO release from implantable medical devices.

SUMMARY OF THE INVENTION

The present invention provides nitric oxide (NO) donating polymers suitable for fabricating and coating medical devices. More specifically, the present invention provides polymers comprising secondary amines that can be diazeniumdiolated and release or donate NO in a controlled manner. Furthermore, the secondary amines discussed above are covalently bound to a sterically hindering group, for example a tert-butyl group.

In one embodiment of the present invention, a nitric oxide donating polymer is provided for coating implantable medical devices comprising a first monomer having a sterically hindered secondary amine group and optionally a second monomer. In another embodiment, the first monomer having a sterically hindered secondary amine group is an acrylate monomer having a sterically hindered secondary amine group and wherein the acrylate monomer is selected from the group consisting of methyl methacrylate, butylmethacrylate, hexyl methacrylate, ethyl methacrylate, 2-(ethoxy ethylmethacrylate), methyl acrylate, ethyl acrylate, hexyl acrylate and butyl acrylate.

In another embodiment, the first monomer having a sterically hindered secondary amine group comprises a secondary amine directly bound to a carbon of a branched alkyl group wherein the branched alkyl group has the structure of Formula 12. In Formula 12, $R_5$, $R_6$, and $R_7$ comprise independent linear or branched alkyl groups with $C_1$ to $C_{10}$.

Formula 12

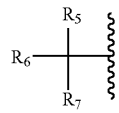

In another embodiment, the steric hindering group is a tert-butyl group having the structure of Formula 13.

tert-Butyl

Formula 13

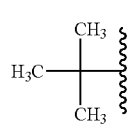

In another embodiment, the second monomer is an acrylate monomer selected from the group consisting of methyl methacrylate, butylmethacrylate, hexyl methacrylate, ethyl methacrylate, 2-(ethoxy ethylmethacrylate), methyl acrylate, ethyl acrylate, hexyl acrylate and butyl acrylate.

In another embodiment of the present invention, a nitric oxide donating polymer is provided for coating implantable medical devices comprising a first monomer having a sterically hindered secondary amine group, optionally a second monomer and optionally a third monomer. In another embodiment, the third monomer is an acrylate monomer selected from the group consisting of methyl methacrylate, butyl methacrylate, hexyl methacrylate, ethyl methacrylate, 2-(ethoxy ethylmethacrylate), methyl acrylate, ethyl acrylate, hexyl acrylate and butyl acrylate In an embodiment of the polymers of the present invention, a nitric oxide donating polymer for coating implantable medical devices is provided wherein the polymer comprises hexyl methacrylate and 2-(tert-butylamino)ethyl methacrylate. In another embodiment, the ratio of hexyl methacrylate to 2-(tert-butylamino)ethyl methacrylate is about 0:100 to about 100:0.

In another embodiment of the polymers of the present invention, the implantable medical device is selected from the group consisting of vascular stents, shunts, vascular grafts, stent grafts, heart valves, catheters, pacemaker leads, and bile duct stents. In one embodiment, the implantable medical device is a vascular stent.

In one embodiment of the present invention, a vascular stent having a nitric oxide donating polymer coating thereon is provided comprising a first monomer having a sterically hindered secondary amine group and optionally a second monomer.

In another embodiment of the present invention, the first monomer having a sterically hindered secondary amine group is an acrylate monomer having a sterically hindered secondary amine group wherein the acrylate monomer is selected from the group consisting of methyl methacrylate, butyl methacrylate, hexyl methacrylate, ethyl methacrylate, 2-(ethoxy ethylmethacrylate), methyl acrylate, ethyl acrylate, hexyl acrylate and butyl acrylate.

In another embodiment, the first monomer having a sterically hindered secondary amine group comprises a secondary amine directly bound to a carbon of a branched alkyl group wherein the branched alkyl group has the structure of Formula 12. In Formula 12, $R_5$, $R_6$, and $R_7$ comprise independent linear or branched alkyl groups with $C_1$ to $C_{10}$.

In another embodiment, the steric hindering group is a tert-butyl group having the structure of Formula 13.

In another embodiment of the present invention, the second monomer is an acrylate monomer selected from the group consisting of methyl methacrylate, butyl methacrylate, hexyl methacrylate, ethyl methacrylate, 2-(ethoxy ethylmethacrylate), methyl acrylate, ethyl acrylate, hexyl acrylate and butyl acrylate.

In another embodiment of the present invention, a vascular stent having a nitric oxide donating polymeric coating thereon is provided comprising a first monomer having a sterically hindered secondary amine group, optionally a second monomer and optionally a third monomer. In another embodiment, the third monomer is an acrylate monomer selected from the group consisting of methyl methacrylate, butyl methacrylate, hexyl methacrylate, ethyl methacrylate, 2-(ethoxy ethylmethacrylate), methyl acrylate, ethyl acrylate, hexyl acrylate and butyl acrylate.

In an embodiment of the vascular stent of the present invention, a nitric oxide donating polymer for coating a vascular stent is provided wherein the polymer comprises hexyl methacrylate and 2-(tert-butylamino)ethyl methacrylate. In another embodiment, the ratio of hexyl methacrylate to 2-(tert-butylamino)ethyl methacrylate is about 0:100 to about 100:0.

DEFINITION OF TERMS 1,4 addition reaction: As described herein, 1,4 addition is the addition of a nucleophile to a α,β unsaturated carbonyl compound at the terminal alkene (Reaction 1). The example presented in Reaction 1 is non-limiting.

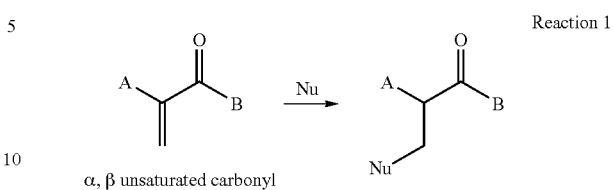

α, β unsaturated carbonyl

Reaction 1

Backbone: As used herein, "backbone" refers to the main chain of a polymer or copolymer of the present invention. A "polyester backbone" as used herein refers to the main chain of a biodegradable polymer comprising ester linkages.

Copolymer: As used herein, a "copolymer" will be defined as a macromolecule produced by the simultaneous chain addition polymerization of two or more dissimilar units such as monomers. Copolymer shall include bipolymers (two dissimilar units), terpolymers (three dissimilar units), etc.

Compatible: As used herein, "compatible" refers to a composition possessing the optimum, or near optimum combination of physical, chemical, biological and drug release kinetic properties suitable for a controlled-release coating made in accordance with the teachings of the present invention. Physical characteristics include durability and elasticity/ductility, chemical characteristics include solubility and/or miscibility and biological characteristics include biocompatibility. The drug release kinetic should be either near zero-order or a combination of first and zero-order kinetics.

Controlled release: As used herein "controlled release" refers to the release of a bioactive compound from a medical device surface at a predetermined rate. Controlled release implies that the bioactive compound does not come off the medical device surface sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments of the present invention an initial burst of drug may be desirable followed by a more gradual release thereafter. The release rate may be steady state (commonly referred to as "timed release" or zero order kinetics), that is the drug is released in even amounts over a predetermined time (with or without an initial burst phase) or may be a gradient release. A gradient release implies that the concentration of drug released from the device surface changes over time.

Glass Transition Temperature (Tg): As used herein "glass transition temperature" or Tg refers to a temperature wherein a polymer structurally transitions from a elastic pliable state to a rigid and brittle state.

$M_n$: As used herein, $M_n$ refers to number-average molecular weight. Mathematically it is represented by the following formula:

$$M_n = \Sigma_i N_i M_i / \Sigma_i N_i,$$

wherein the $N_i$ is the number of moles whose weight is $M_i$.

$M_w$: As used herein, $M_w$ refers to weight average molecular weight that is the average weight that a given polymer may have. Mathematically it is represented by the following formula:

$$M_w = \Sigma_i N_i M_i^2 / \Sigma_i N_i M_i,$$

wherein $N_i$ is the number of molecules whose weight is $M_i$.

Sterically hindered amine: As used herein, "sterically hindered amine" refers to amines whose substitution on the carbon(s) adjacent to the amine nitrogen is such that the spatial environment of the carbon(s) encumbers the spatial environment of the amine.

DETAILED DESCRIPTION OF THE INVENTION

The present invention provides nitric oxide (NO)-donating polymers suitable for coating medical devices. More specifically, the present invention provides polymers comprising secondary amines that can be diazeniumdiolated and release NO in a controlled manner. Even more specifically, the secondary amines are covalently bound to a sterically hindering group, for example a tert-butyl group.

In the synthesis of acrylate-based polymers having secondary amine groups, long synthetic routes are required. These long synthetic routes are associated with problems including unwanted reactions when secondary amines are present with unsaturated ketones or esters. Addition of secondary amines to α,β unsaturated esters can result in at least two reaction products: 1,4 additions to the alkene and the formation of amides resulting from direct attack on the ester carbonyl. In order to eliminate the unwanted reactions possible in polymerization, suitable monomers are required. In the synthesis of the monomers, the secondary amines must be protected and subsequently de-protected after polymerization of the monomers is complete. The de-protected amine can attack the ester carbonyl and yield an amide. Consequently, these secondary amines are not available to form diazeniumdiolates. In the present invention, polymers comprising secondary amines directly bonded to sterically hindering groups largely eliminate side reactions and allow for facile synthesis of NO donating polymers.

The polymers of the present invention are synthesized using methods that circumvent the protection and de-protection steps for secondary amines which are common in the synthesis of like polymers. Increasing the steric bulk surrounding the secondary amine prevents unwanted 1,4 addition reactions of the amine to the acrylic monomer. As described herein, a 1,4 addition is the addition of a nucleophile to a α,β unsaturated carbonyl compound at the terminal alkene. Other side reactions, such as attack of the amine on the ester to form an amide are also prevented by the surrounding hindering group.

In one embodiment of the present invention, an exemplary NO donating polymer comprises the general chemical structure as depicted in Formula 3. In another embodiment of the present invention, the polymer comprises a copolymer. An exemplary copolymer is depicted in Formula 4.

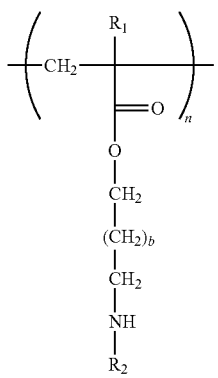

Formula 3

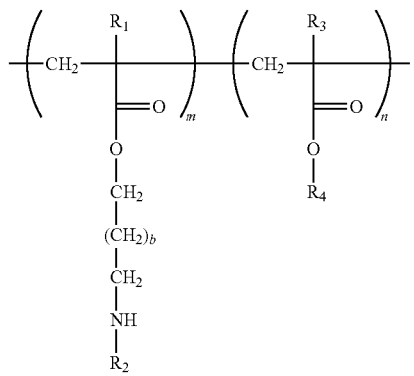

Formula 4

In Formulas 3 and 4 the R groups are defined as a general chemical moiety and not intended to limit the scope of the invention. Moreover, in Formulas 3 and 4, n and m are integers between about 2 and about 25,000 and b is an integer between 0 and 20. The sum of m and n is at least 2. For example, and not intended as limitations; $R_1$, $R_3$ and $R_4$ comprise straight chain alkyl groups ranging from about 1 carbon to about 25 carbons, cyclic alkyl groups with rings sizes ranging from about 3 carbons to about 8 carbons, heterocycles with ring sizes ranging from about 2 carbons to about 8 carbons, alkenyl groups, or poly alkenyl groups, or branched alkyl with carbons ranging from about 3 carbons to about 25 carbons, branched ethers, straight chain ethers, branched and straight chain thio-ethers, or branched and straight chain sulfamides, or branched and straight chain sulfones, or branched and straight chain phosphates, branched and straight chain phosphoryl amides, or branched and straight chain internal alkynes, branched and straight chain terminal alkynes, branched and straight chain amides, branched and straight chain esters, branched and straight chain ketones or any combination thereof. The steric hindering group, $R_2$, comprises highly branched alkyl groups such as tert-butyl. In one embodiment, wherein b=0, the monomer is 2-ethoxy ethyl methacrylate.

In an embodiment of the polymers of Formula 3 of the present invention, the sterically hindered secondary amine-containing polymer comprises acrylic monomers having sterically hindered secondary amine groups wherein the acrylic monomer includes, but not limited to, methyl methacrylate, methyl butylmethacrylate, butyl methacrylate, hexyl methacrylate, ethyl acrylate, 2-(ethoxy ethylmethacrylate), methyl acrylate, ethyl acrylate, hexyl acrylate and butyl acrylate.

In an embodiment of the polymers of Formula 4 of the present invention, the sterically hindered secondary amine-containing polymer comprises acrylic monomers having sterically hindered secondary amine groups wherein the acrylic monomer includes, but not limited to, methyl methacrylate, methyl butylmethacrylate, butyl methacrylate, hexyl methacrylate, ethyl acrylate, 2-(ethoxy ethylmethacrylate), methyl acrylate, ethyl acrylate, hexyl acrylate and butyl acrylate. In another embodiment of the polymers of Formula 4 of the present invention, the non-sterically hindered secondary amine-containing polymer comprises acrylic monomers including, but not limited to, methyl methacrylate, methyl butylmethacrylate, butyl methacrylate, hexyl methacrylate, ethyl acrylate, 2-(ethoxy ethylmethacrylate), methyl acrylate, ethyl acrylate, hexyl acrylate and butyl acrylate.

In one embodiment of the present invention, the steric hindering group, $R_2$, comprises a highly branched alkyl group having the structure of Formula 12 with $R_5$, $R_6$, and $R_7$ comprising independent linear or branched alkyl groups with $C_1$ to $C_{10}$. In a non-limiting example, $R_2$ comprises a tert-butyl group (Formula 13).

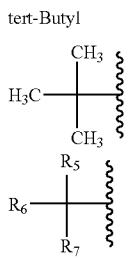

With regard to Formula 4, the ratio of m to n is between about 0:100 and about 100:0. In particular embodiments of the polymers of the present invention, the ratio of m to n is more than about 0:100, 10:90, 20:80, 30:70, 40:60, 50:50; 60:40, 70:30, 80:20 and 90:10.

Furthermore with regards to Formulas 3 and 4, variations in the chain length (tether) of the amine, i.e. increasing b, can be produced by esterification of acrylic acids. The reaction scheme below depicts the synthesis of Formula 8 wherein b is an integer from 0 to about 20. Formula 6 is readily available from standard synthetic manipulations of Formula 5. Hydrogenation of Formula 6 with palladium on carbon with hydrogen yields the amino alcohol of Formula 7. Esterification of Formula 7 with an acrylate such as but not limited to acrylic acid, under acidic conditions provides the monomer of Formula 8. As would be recognized by persons skilled in the art of polymer synthesis the synthetic approach described above is general, it is one non-limiting method of synthesizing monomers of Formula 8

The secondary amine as discussed with regard to the polymers of the present invention is directly bound to sterically encumbering molecular moieties that are hindering side reactions by the amine. During the polymerization reactions of acrylate monomers, amines in one monomer can undergo 1,4 additions to another acrylate monomer. Formation of amides from the attack of the secondary amine on the acrylate ester (both in the monomer and the polymer) is also largely prevented by steric hindrances. In the invention disclosed herein, NO donating polymers suitable for coating medical devices comprise secondary amines directly bonded to sterically encumbering moieties. In one embodiment of the present invention the polymers comprise an acrylic backbone, a backbone of the general form, Formula 9:

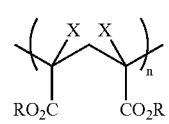

Formula 9 wherein R and X represent functional groups.

In one embodiment of the present invention, a polymer comprises the Formula 3, wherein $R_1$ is methyl, $R_2$ is tert-butyl and b is 0. The synthesis of this exemplary polymer is described further in Example 1.

In another embodiment of the present invention a polymer comprises Formula 4, $R_1$ is methyl, $R_2$ is tert-butyl, $R_3$ is methyl, $R_4$ is n-butyl and b is 0. The ratio of m:n ranges from about 0:100 to about 100:0. In one embodiment, the ratio of m to n is about 73:27. In yet another embodiment the ratio of m to n is about 43:57. In still another embodiment the ratio of m to n is about 19:81.

The polymeric coatings of the present invention have hindered secondary amine groups that can form diazeniumdiolates and, upon exposure to a physiological medium, release

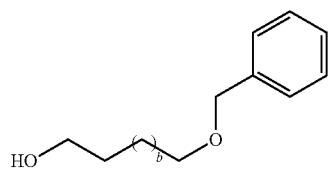
Formula 5

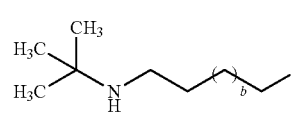
Formula 6

Pd/C
H₂

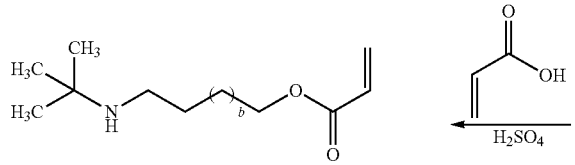
Formula 8

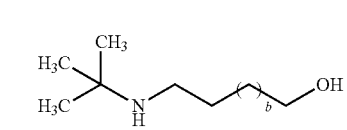
Formula 7

NO. A non-limiting example of diazeniumdiolates of the present invention is provided in Formula 10:

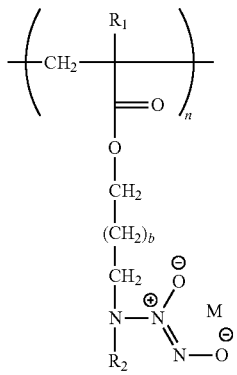

Formula 10 wherein n is an integer between about 2 to about 25,000, b is an integer between 0 and about 20 and M is a metal or other cationic molecule with the appropriate charge.

Still another non-limiting example of diazeniumdiolates of the present invention is provided in Formula 11:

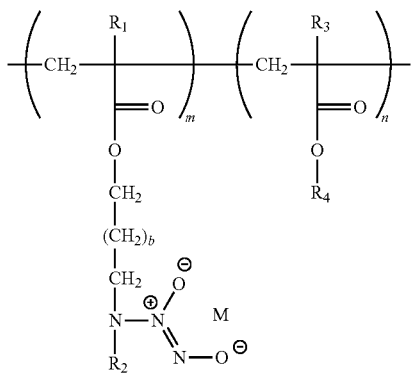

Formula 11 wherein n and m is an integer between about 2 and about 25,000 and b is an integer between 0 and about 20.

Physical properties of the polymers in the present invention can be fine tuned so that the polymers can optimally perform for their intended use. Properties that can be fine tuned, without limitation, include Tg, molecular weight (both $M_n$ and $M_w$), polydispersity index (PDI, the quotient of $M_w/M_n$), degree of elasticity and degree of amphiphlicity. In one embodiment of the present invention, the Tg of the polymers range from about −10° C. to about 85° C. In still another embodiment of the present invention, the PDI of the polymers range from about 1.35 to about 4. In another embodiment of the present invention, the Tg of the polymers ranges form about 0° C. to about 40° C. In still another embodiment of the present invention, the PDI of the polymers range from about 1.5 to about 2.5.

The polymeric coatings of the present invention are intended for medical devices deployed in a hemodynamic environment and possess excellent adhesive properties. That is, the coating must be stably linked to the medical device surface. Many different materials can be used to fabricate the implantable medical devices including, but not limited to, stainless steel, nitinol, aluminum, chromium, titanium, gold, cobalt, ceramics, and a wide range of synthetic polymeric and natural materials including, but not limited to, collagen, fibrin and plant fibers. All of these materials, and others, may be used with the polymeric coatings made in accordance with the teachings of the present invention. Furthermore, the polymers of the present invention can be used to fabricate an entire medical device.

There are many theories that attempt to explain, or contribute to our understanding of how polymers adhere to surfaces. The most important forces include electrostatic and hydrogen bonding. However, other factors including wettability, absorption and resiliency also determine how well a polymer will adhere to different surfaces. Therefore, polymer base coats, or primers are often used in order to create a more uniform coating surface.

The NO donating polymeric coatings of the present invention can be applied to medical device surfaces, either primed or bare, in any manner known to those skilled in the art. Applications methods compatible with the present invention include, but are not limited to, spraying, dipping, brushing, vacuum-deposition, and others. Moreover, the NO donating polymeric coatings of the present invention may be used with a cap coat. A cap coat as used herein refers to the outermost coating layer applied over another coating. A NO donating polymer coating of the present invention is applied over the primer coat. Then, a polymer cap coat is applied over the NO donating polymeric coating of the present invention. The cap coat may optionally serve as a diffusion barrier to control the NO release. The cap coat may be merely a biocompatible polymer applied to the surface of the sent to protect the stent and have no effect on the NO release rates.

EXAMPLES

Example 1

Example 1 is illustrative of the synthesis of a polymer having secondary amines directly bound to a sterically hindered moiety.

To a 500 mL three-neck round bottom glass equipped with a mechanical stirrer is added 2-(tert-butylamino)ethyl methacrylate (10 g, 0.54 mmol) in a mixture of n-propyl alcohol and 2-butanone (70:30, 2-butanone:n-propyl alcohol, 300 mL) and 2,2'-azobis(2-methylpropionitrile) (0.8 g, 0.8 wt. %). A net positive pressure of nitrogen is introduced and the reaction heated (60° C.) for 5 hours. Then the reaction is allowed to cool (23° C.). The polymer solution is poured into cold methanol (−60° C.) and a white polymer is precipitated out. All the solvents are decanted and the polymer is re-dissolved in chloroform. This procedure is repeated three times. Then, the polymer is placed in vacuum and the solvent removed in vacuo, yielding the solid polymer.

Example 2

Example 2 is illustrative of the synthesis of a co-polymer having secondary amines directly bound to a sterically hindered moiety.

To a 500 mL three-neck round bottom glass equipped with a mechanical stirrer is added 2-(tert-butylamino)ethyl methacrylate (10 g, 0.54 mmol), n-butyl methacrylate (7.67 g, 0.54 mmol) in a mixture of n-propyl alcohol and 2-butanone (70:30, 2-butanone:n-propyl alcohol, 300 ml) and 2,2'-azobis(2-methylpropionitrile) (1.36 g, 0.8 wt. %). A net positive pressure of nitrogen is introduced and the reaction heated (60° C.) for 5 hours. Then the reaction is allowed to cool (23° C.). The polymer solution is poured into cold methanol (−60° C.) and a white polymer is precipitated out. All the solvents are decanted and the polymer is re-dissolved in chloroform. This procedure is repeated three times. Then, the polymer is placed in vacuum and the solvent removed in vacuo, yielding the solid polymer Example 3

Example 3 is illustrative of the formation of diazeniumdiolates, i.e. incorporation of nitric oxide (NO) in the polymer.

Polymers dissolved (typically 10 mg/50 ml) in THF are placed in a high pressure reaction vessel. An inert gas (including, but not limited to, argon and nitrogen) is then purged through the vessel. A base dissolved in a solvent (typically sodium methoxide or potassium methoxide in methanol) are then added in excess (typically 110% to 200%). The reaction is allowed to stir and the vessel purged with NO gas. The pressure of NO gas is increased (typically at least 15 psi) and the reaction mixture is then stirred further for at least 24 hours. At the end of the required time for the formation of diazeniumdiolates, dry hydrophobic solvents (typically hexanes or methyl tert-butyl ether) are added to aid in the precipitation of the polymers. The polymers are then filtered and dried.

Example 4

Example 4 is illustrative of the formation of diazeniumdiolates on vascular stents coated with the polymers of the present invention.

A vascular stent coated with at least one polymer from Examples 3 and 4 is placed in a 13 mm×100 mm glass test tube. Ten milliliters of 3% sodium methoxide in methanol or acetonitrile is added to the test tube, which is then placed in a 250 mL stainless steel Parr® apparatus. The apparatus is degassed by repeated cycles (×10) of pressurization/depressurization with nitrogen gas at 10 atmospheres. Next, the vessel undergoes 2 cycles of pressurization/depressurization with NO at 30 atmospheres. Finally, the vessel is filled with NO at 30 atmospheres and left at room temperature for 24 hrs. After 24 hrs, the vessel is purged of NO and pressurized/depressurized with repeated cycles (×10) of nitrogen gas at 10 atmospheres. The test tube is removed from the vessel and the 3% sodium methoxide solution is decanted. The stent is then washed with 10 mL of methanol (×1) and 10 mL of diethyl ether (×3). The stent is then removed from the test tube and dried under a stream of nitrogen gas. This procedure results in a diazeniumdiolated polymer-coated vascular stent.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An implantable medical device comprising an NO-releasing polymer coating comprising:
a first monomer comprising a diazeniumdiolate group prepared from a sterically hindered secondary amine group; and
optionally a second monomer;

wherein the polymer releases NO in a controlled manner upon contact with a biological environment.

2. The implantable devices of claim 1 wherein said first monomer is prepared from a monomer selected from the group consisting of methyl methacrylate, butyl methacrylate, hexyl methacrylate, ethyl methacrylate, 2-(ethoxy ethylmethacrylate), methyl acrylate, ethyl acrylate, hexyl acrylate and butyl acrylate, each being substituted with a sterically hindered secondary amine group.

3. The implantable medical device of claim 2 wherein said monomer having a sterically hindered secondary amine group comprises a secondary amine directly bound to a carbon of a branched alkyl group wherein said branched alkyl group has the structure of Formula 12, and wherein $R_5$, $R_6$, and $R_6$ are independent linear or branched alkyl groups with $C_1$ to $C_{10}$.

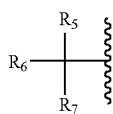

Formula 12

4. The implantable medical devices of claim 3 wherein said branched alkyl group is a tert-butyl group having the structure of Formula 13.

tert-Butyl

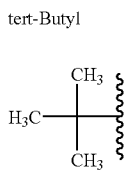

Formula 13

5. The implantable medical devices of claim 1 wherein said second monomer is an acrylate monomer selected from the group consisting of methyl methacrylate, butyl methacrylate, hexyl methacrylate, ethyl methacrylate, 2-(ethoxy ethylmethacrylate), methyl acrylate, ethyl acrylate, hexyl acrylate and butyl acrylate.

6. The implantable medical device of claim 1 further comprising a third monomer.

7. The implantable medical device of claim 6 wherein said third monomer is an acrylate monomer selected from the group consisting of methyl methacrylate, butyl methacrylate, hexyl methacrylate, ethyl methacrylate, 2-(ethoxy ethylmethacrylate), methyl acrylate, ethyl acrylate, hexyl acrylate and butyl acrylate.

8. The implantable medical device of claim 1 wherein said first monomer is prepared from 2-(tert-butylamino)ethyl methacrylate and said second monomer is hexyl methacrylate.

9. The implantable medical device of claim 1 wherein said implantable medical device is selected from the group consisting of vascular stents, shunts, vascular grafts, stent grafts, heart valves, catheters, pacemaker leads, and bile duct stents.

10. The implantable medical device of claim 9 wherein said implantable medical device is a vascular stent.

11. A vascular stent comprising an NO-releasing polymer coating comprising:
a first monomer comprising a diazeniumdiolate group prepared from a sterically hindered secondary amine group; and
optionally a second monomer;
wherein the polymer releases NO in a controlled manner upon contact with a biological environment.

12. The vascular stent having a coating of claim 11 wherein said first monomer is prepared from a monomer selected from the group consisting of methyl methacrylate, butyl methacrylate, hexyl methacrylate, ethyl methacrylate, 2-(ethoxy ethylmethacrylate), methyl acrylate, ethyl acrylate, hexyl acrylate and butyl acrylate, each being substituted with a sterically hindered secondary amine group.

13. The vascular stent of claim 12 wherein said monomer having a sterically hindered secondary amine group comprises an secondary amine directly bound to a carbon of a branched alkyl group wherein said branched alkyl group has the structure of Formula 12, and wherein $R_5$, $R_6$, and $R_6$ are independent linear or branched alkyl groups with $C_1$ to $C_{10}$.

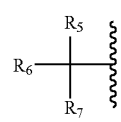

Formula 12

14. The vascular stent having a coating of claim 13 wherein said branched alkyl group is a tert-butyl group having the structure of Formula 13.

tert-Butyl

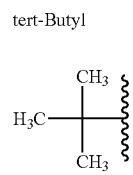

Formula 13

15. The vascular stent having a coating of claim 11 wherein said second monomer is an acrylate monomer selected from the group consisting of methyl methacrylate, butyl methacrylate, hexyl methacrylate, ethyl methacrylate, 2-(ethoxy ethylmethacrylate), methyl acrylate, ethyl acrylate, hexyl acrylate and butyl acrylate.

16. The vascular stent having a coating of claim 11 further comprising a third monomer.

17. The vascular stent having a coating of claim 16 wherein said third monomer is an acrylate monomer selected from the group consisting of methyl methacrylate, butyl methacrylate, hexyl methacrylate, ethyl methacrylate, 2-(ethoxy ethylmethacrylate), methyl acrylate, ethyl acrylate, hexyl acrylate and butyl acrylate and combinations thereof.

18. The vascular stent having a coating of claim 11 wherein said first monomer is prepared from 2-(tert-butylamino)ethyl methacrylate and said second monomer is hexyl methacrylate.

19. A vascular stent comprising an NO-releasing polymer coating comprising:
a first monomer comprising a diazeniumdiolate group prepared from a sterically hindered secondary amine group comprising a secondary amine directly bound to a carbon of a branched alkyl group wherein said branched alkyl group has the structure of Formula 12, and wherein $R_5$, $R_6$, and $R_6$ are independent linear or branched alkyl groups with $C_1$ to $C_{10}$

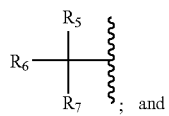
Formula 12
; and
a second monomer selected from the group consisting of methyl methacrylate, butyl methacrylate, hexyl methacrylate, ethyl methacrylate, 2-(ethoxy ethylmethacrylate), methyl acrylate, ethyl acrylate, hexyl acrylate and butyl acrylate;
wherein the polymer releases NO in a controlled manner upon contact with a biological environment.
* * * * *